United States Patent
Garner et al.

(10) Patent No.: US 9,044,439 B2
(45) Date of Patent: *Jun. 2, 2015

(54) LOW DOSE LIPOIC AND PHARMACEUTICAL COMPOSITIONS AND METHODS

(75) Inventors: William Garner, Eastport, ME (US); Margaret Garner, Eastport, ME (US)

(73) Assignee: Encore Health, LLC, Roanoke, VA (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/267,208

(22) Filed: Nov. 7, 2008

(65) Prior Publication Data

US 2009/0227677 A1    Sep. 10, 2009

Related U.S. Application Data

(60) Provisional application No. 61/033,870, filed on Mar. 5, 2008, provisional application No. 61/060,487, filed on Jun. 11, 2008, provisional application No. 61/077,186, filed on Jul. 1, 2008.

(51) Int. Cl.
*A61K 31/35* (2006.01)
*A61K 31/19* (2006.01)

(52) U.S. Cl.
CPC ..................................... *A61K 31/19* (2013.01)

(58) Field of Classification Search
USPC .................................................. 514/439, 440
See application file for complete search history.

(56) References Cited

U.S. PATENT DOCUMENTS

| | | | |
|---|---|---|---|
| 3,238,224 A | 3/1966 | Ohara et al. | |
| 3,855,240 A | 12/1974 | Mueller | |
| 4,210,667 A | 7/1980 | Sarges et al. | |
| 4,755,528 A | 7/1988 | DuPriest et al. | |
| 5,395,356 A | 3/1995 | King et al. | |
| 5,459,133 A | 10/1995 | Neufeld | |
| 5,465,737 A | 11/1995 | Schachar | |
| 5,466,680 A | 11/1995 | Rudy | |
| 5,476,515 A | 12/1995 | Kelman et al. | |
| 5,488,050 A | 1/1996 | Neufeld | |
| 5,503,165 A | 4/1996 | Schachar | |
| 5,527,774 A | 6/1996 | Girard | |
| 5,529,076 A | 6/1996 | Schachar | |
| 5,624,955 A | 4/1997 | Nagasawa et al. | |
| 5,665,770 A | 9/1997 | Terao et al. | |
| 5,686,450 A | 11/1997 | Hellberg et al. | |
| 5,688,828 A | 11/1997 | Hellberg et al. | |
| 5,691,379 A | 11/1997 | Ulrich et al. | |
| 5,722,952 A | 3/1998 | Schachar | |
| 5,817,630 A | 10/1998 | Hofmann et al. | |
| 5,843,184 A | 12/1998 | Cionni | |
| 5,869,468 A | 2/1999 | Freeman | |
| 5,874,455 A | 2/1999 | Terao et al. | |
| 5,888,243 A | 3/1999 | Silverstrini | |
| 6,007,510 A | 12/1999 | Nigam | |
| 6,013,462 A | 1/2000 | Kauvar et al. | |
| 6,030,950 A | 2/2000 | Ohlenschlager | |
| 6,063,116 A | 5/2000 | Kelleher | |
| 6,214,044 B1 | 4/2001 | Silverstrini | |
| 6,288,106 B1 | 9/2001 | Pearson et al. | |
| 6,313,164 B1 | 11/2001 | Fujita et al. | |
| 6,339,102 B1 | 1/2002 | Meyerhoff et al. | |
| 6,387,945 B2 | 5/2002 | Packer et al. | |
| 6,472,541 B2 | 10/2002 | Tsien et al. | |
| 6,664,287 B2 | 12/2003 | Avery et al. | |
| 6,703,039 B2 | 3/2004 | Xia et al. | |
| 6,743,779 B1 | 6/2004 | Unger et al. | |
| 6,923,955 B2 | 8/2005 | Till et al. | |
| 7,164,943 B2 | 1/2007 | Roy | |
| 7,914,815 B2 | 3/2011 | Till et al. | |
| 7,935,332 B2 | 5/2011 | Till | |
| 8,147,816 B2 | 4/2012 | Till et al. | |
| 8,410,162 B2 | 4/2013 | Garner et al. | |
| 8,647,612 B2 | 2/2014 | Garner et al. | |
| 8,697,109 B2 | 4/2014 | Garner et al. | |
| 2002/0025311 A1 | 2/2002 | Till | |
| 2002/0035243 A1 | 3/2002 | Imfeld et al. | |
| 2003/0187058 A1 | 10/2003 | Hasselwander et al. | |
| 2003/0228299 A1 | 12/2003 | Droy-Lefaix et al. | |
| 2004/0044227 A1 | 3/2004 | Klatt et al. | |
| 2004/0092586 A1 | 5/2004 | Ogata et al. | |
| 2005/0101677 A1 | 5/2005 | Till | |
| 2005/0112113 A1 | 5/2005 | Till et al. | |
| 2005/0130881 A1 | 6/2005 | Shashoua | |
| 2005/0137124 A1 | 6/2005 | Castillejos | |

(Continued)

FOREIGN PATENT DOCUMENTS

| | | |
|---|---|---|
| EP | 0 369 880 | 5/1990 |
| WO | WO 93/25166 | 12/1993 |

(Continued)

OTHER PUBLICATIONS

Ip C, Ganther HE. 1992. Comparison of selenium and sulfur analogs in cancer prevention. Carcinogenesis. 13(7): 1167-70.
U.S. Appl. No. 12/815,586, filed Jun. 15, 2010, Garner et al.
U.S. Appl. No. 12/815,526, filed Jun. 15, 2010, Garner et al.
Bustamante, J., et al., 1998. α-Lipoic Acid in Liver Metabolism and Disease. *Free Radical Biology & Medicine* 24: No. 6 1023-1039.
Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.
Giblin FJ, et al. 1979. The effects of X-irradiation on lens reducing systems. Investigative Ophthalmology & Visual Science 18:468-475.
Kramár P, et al. 1987. Thermal cataract formation in rabbits. NCBI Pubmed abstract, PMID: 3426637, abstract of Bioelectromagnetics 8:397-406.

(Continued)

*Primary Examiner* — Zohreh Fay
(74) *Attorney, Agent, or Firm* — Sterne, Kessler, Goldstein & Fox PLLC

(57) ABSTRACT

Compositions containing low doses of lipoic acid-based active agents and methods for using the same are provided. In particular, compositions containing low dose lipoic acid, lipoic acid derivatives, and lipoic acid seleno-derivatives and are provided to prevent and/or treat ocular diseases.

6 Claims, 5 Drawing Sheets

(56) References Cited

U.S. PATENT DOCUMENTS

| | | |
|---|---|---|
| 2005/0171212 A1 | 8/2005 | Gierhart et al. |
| 2005/0287201 A1 | 12/2005 | Till et al. |
| 2006/0177430 A1 | 8/2006 | Bhushan |
| 2006/0188492 A1 | 8/2006 | Richardson et al. |
| 2007/0055070 A1 | 3/2007 | Lawrence et al. |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0139990 A1 | 6/2008 | Till et al. |
| 2008/0213239 A1 | 9/2008 | Morris |
| 2009/0082281 A1 | 3/2009 | Shashoua |
| 2009/0093541 A1 | 4/2009 | Ogata |
| 2009/0124683 A1 | 5/2009 | Garner et al. |
| 2009/0192212 A1 | 7/2009 | Garner et al. |
| 2010/0098653 A1 | 4/2010 | Yu et al. |
| 2010/0317608 A1 | 12/2010 | Garner et al. |
| 2011/0135622 A1 | 6/2011 | Till et al. |
| 2014/0121266 A1 | 5/2014 | Garner et al. |

FOREIGN PATENT DOCUMENTS

| | | |
|---|---|---|
| WO | WO 93/25199 | 12/1993 |
| WO | WO 94/01773 | 1/1994 |
| WO | WO 02/13863 | 2/2002 |
| WO | WO 02056804 | 7/2002 |
| WO | WO 03/084532 | 10/2003 |
| WO | WO 2004/028536 | 4/2004 |
| WO | WO 2005/084635 | 9/2005 |
| WO | WO 2006/047080 | 5/2006 |
| WO | WO 2007011874 | 1/2007 |
| WO | WO 2008/120070 | 10/2008 |
| WO | WO 2010054135 | 5/2010 |
| WO | WO 2010147962 | 12/2010 |

OTHER PUBLICATIONS

Li, X., Liu, Z., et al. 2008. Lipoamide protects retinal pigment epithelial cells from oxidative stress and mitochondrial *Free Radic Biol Med.* 44(7): 1465-1474.

Lipman RM, et al. 1988. Cataracts induced by Microwave and Ionizing Radiation. NCBI Pubmed abstract, PMID: 3068822, abstract of Surv. Ophthalmol 33:200-210.

Trayhurn P. and Van Heyningen R. 1973. The Metabolism of Amino Acids in the Bovine Lens; Their Oxidation as a Source of Energy. *Biochem. J.* 136:67-75.

Wakabayashi, Y. et al. 2006. Glutamate Levels in Aqueous Humor of Patients with Retinal Artery Occlusion. *Retina* 26:432-436.

Zwingmann, C. et al. 2001. $^{13}$C Isotopomer Analysis of Glucose and Alanine Metabolism Reveals Cytosolic Pyruvate Compartmentation as Part of Energy Metabolism in Astrocytes. *GLIA* 34:200-212.

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. *Experimental eye research* 72:199-214.

Applegate, M. A., K. M. Humphries, and L. I. Szweda 2007. Reversible Inhibition of alpha-Ketoglutarate Dehydrogenase by Hydrogen Peroxide: Glutathionylation and Protection of Lipoic Acid. *Biochemistry*.

Argirova, M., M. Kleine-Reidick, and W. Breipohl. 2004. Redox status of the eye lens: a regional study. *Cell biochemistry and biophysics* 41: 381-390.

Ariga T, et al. 2000. Antithrombotic and antineoplastic effects of phyto-organosulfur compounds. Biofactors, 13(1-4):251-5.

Arora A, et al. 2004, Reversal of P-glycoprotein-mediated rnullidrug resistance by diallyl sulfide in K562 leukemic cells and in mouse liver. Carcinogenesis. 25(6):941-9. Epub Jan. 16, 2004.

Asmellash S, et al. 2005. Modulating the endoplastic reticulum stress response with trans-4,5-dihydroxy-1,2-dithiane prevents chemically induced renal injury in vivo, Toxicol Sci. 88(2):576-84. Epub Sep. 8, 2005.

Baghieri, S., and M. H. Garner, 1992. Na,K-ATPase and phospholipid degradation in bovine and human lenses. *Current eye research* 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.

Bilska, A. and L. Wlodek. 2005. Lipoid acid—the drug of the future? *Pharmacol Rep* 57: 570-577.

Bilska, A., M. Dubiel, M. Sokolowska-Jezewicz, E. Lorenc-Koci, and Wlodek. 2007, Alpha-lipoic acid differently affects the reserpine-induced oxidative stress in the striatum and prefrontal cortex of rat brain. *Neuroscience* 146: 1758-1771.

Bitar, M. S., S. Wahid, C. W. Pilcher, E. Al-Saieh, and F. Al-Mulla, 2004. Alpha-lipoic acid mitigates insulin resistance in Goto-Kakizaki rats, *Hormone and metabolic research. Hormon—und Stoffwechselforschung* 36: 542-549.

Bianco, R. A., T. R. Ziegler, B. A. Carlson, P. Y. Cheng, Y. Park, G. A. Cotsonis, C. J. Accardi, and D. P. Jones, 2007, Diurnal variation in glutathione and cysteine redox states in human plasma. *The American journal of clinical nutrition* 86: 1016-1023.

Blankenship, T. N., J. F. Hess, and P. G. FitzGerald. 2001, Development- and differentiation-dependent reorganization of intermediate filaments in fiber cells. *Investigative ophthalmology & visual science* 42: 735-742.

Bonomi, L et al. 1990. Evaluation of the 701 interzeag lens opacity meter. Graefe's Arch Clin Exp Ophthalmol 228(5):447-9.

Borja, D et al. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992 Membrane-binding properties of filensin, a cytoskeletal protein of the lens fiber cells. *Journal of cell science* 103 ( Pt 3): 709-718.

Cenedella, R. J. 1998. Prenylation of proteins by the intact lens. *Investigative ophthalmology & visual science* 39: 1276-1280.

Croft, M. A., A. Glasser, G. Heatley, J. McDonald, T. Ebbert, N. V. Nadkarni, and P. L. Kaufman, 2006. The zonula, lens, and circumlental space in the normal indectomized rhesus monkey eye. *Investigative ophthalmology & visual science* 47: 1087-1095.

Croft, M. A., and P. L. Kaufman. 2006. Accommodation and presbyopia: the cillary neuromuscular view. *Ophthalmology clinics of North America* 19: 13-24, v.

Dubbelman, M., G. L. Van der Heijde, H. A. Weeber, and G. F. Vrensen. 2003. Changes in the internal structure of the human crystalline lens with age and accommodation. *Vision research* 43: 2363-2375.

Eason, R. C., H. E. Archer, S. Akhtar, and C. J. Bailey. 2002. Lipoic acid increases glucose uptake by skeletal muscles of obese-diabetic ob/ob mice. *Diabetes Obes Metab* 4: 29-35.

Egan, D., P. James, D. Cooke, and R. O'Kennedy. 1997, Studies on the cytostatic and cytotoxic effects and mode of action of 8-nitro-7-hydroxycoumarin. *Cancer letters* 118: 201-211.

Finn, G., B. Creaven, and D. Egan. 2003 Modulation of mitogen-activated protein kinases by 6-nitro-7-hydroxycoumarin mediates apoptosis in renal carcinoma cells. *European journal of pharmacology* 481: 159-167.

Finn, G. J., B. S. Creaven, and D. A. Egan. 2004. A study of the role of cell cycle events mediating the action of coumarin derivatives in human malignant melanoma cells. *Cancer letters* 214: 43-54.

Flammer J, Bebie H. 1987. Lens Opacity Meter: a new instrument to quantify lens opacity. Ophthalmologica 195(2):69-72.

Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. *Proceedings of the National Academy of Sciences of the United States of America* 96: 1193-1200.

Gail MH & You WC. 2006. A factorial trial including gailic supplements assesses effect in reducing precancerous gastric lesions. J Nutr. 136(3 Suppl):813S-815S.

Garner, M. H., and J. Horwitz. 1994. Catalytic subunit isoforms of mammalian lens Na,K-ATPase. *Current eye research* 13: 65-77.

Garner, M. H., and Y. Kong. 1999. Lens epitheilum and fiber Na,K-ATPases: distribution and localization by immunocytochemistry. *Investigative ophthamology & visual science* 40: 2291-2298.

(56) References Cited

OTHER PUBLICATIONS

Garner, M. R. and J. R. Kuszak. 1993. Cations, oxidants, light as causative agents in senile cataracts. *Puerto Rico health sciences journal* 12: 115-122.

Garner, M. H., and A. Spector. 1980. Selective oxidation of cysteine and methionine in normal and senile cataractous lenses. *Proceedings of the National Academy of Sciences of the United States of America* 77: 1274-1277.

Garner, M. H. 1994, Na,K-ATPases of the lens epithelium and fiber cell: formation of catalytic cycle intermediates and Na+: K+ exchange. *Experimental eye research* 58: 705-718.

Gilmore WJ & Kirby GM, 2004. Endoplasmic reticulum stress due to altered cellular redox status positively regulates murine hepatic CYP2A5 expression. J Pharmacol Exp Ther. 308(2):600-8. Epub Nov. 10, 2003.

Glasser, A., and M. C. Campbell. 1999, Biometric, optical and physical changes in the isolated human crystalline lens with age in relation to presbyopia. *Vision research* 39: 1991-2015.

Goulielmos, G., F. Gounari, S. Remington. S, Muller, M. Haner, U. Aebi, and S. D. Georgatos. 1996. Filensin and phakinin form a novel type of beaded intermediate filaments and coassemble de novo in cultured cells. *The Journal of cell biology* 132: 643-655.

Goulielmos, G., S. Remington, F. Schwesinger, S. D. Georgatos, and F. Gounari, 1996. Contributions of the structural domains of filensin in polymer formation and filament distribution. *Journal of cell science* 109 ( Pt 2): 447-456.

Green DR & Reed JC. 1998. Mitochondria and apoptosis. Science 281(5381):1309-12.

Gruzman, A., A. Hidmi, J. Katzhendler, A. Haj-Yehie, and S. Sasson. 2004. Synthesis and characterization of new and potent alpha-lipoic acid derivatives. *Bioorganic & medicinal chemistry* 12: 1183-1190.

Guest, P. C., H. A. Skynner, K. Salim, F. D. Tattersall, M. R. Knowles, and J. R. Atack. 2006. Detection of gender differences in rat lens proteins using 2-D-DIGE, *Proteomics* 6: 667-676.

Gurney, AM. 1994. Flash photoiysis of caged compounds in *Microelectrode Techniques,* ed Ogden D, pp. 389-406.

Hathal M. et al. 2004. Iontophoresis: from the lab to the bed side. Exp Eye Res 78(3):751-57.

Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.

Heidemann, S. R., S. Kaech, R. E. Buxbaum, and A. Matus, 1999. Direct observations of the mechanical behaviors of the cytoskeleton in living fibroblasts. *The Journal of cell biology* 145:109-122.

Hardie, R.C. 1995. Photolysis of Caged $Ca^{2+}$ Facilitates and inactivates but Does Not Directly Excite Light-Sensitive Channels in *Drosophila* Photoreceptors. The Journal of Neuroscience 15(1):899-902.

Hermans E., M. Dubbelman, R. van der Heijde, and R. Heethaar. 2007. The shape of the human lens nucleus with accommodation. *Journal of vision* 7: 16 11-10.

Hoenders, H.J., et al. "Lens proteins and aging" J Gerontol (May 1993) 38(3):278-86.

Hofmann, M., P. Manika H. Tritschler, J. Fuchs, and G. Zimmer. 1995. Decrease of red cell membrane fluidity and -SH groups due to hyperglycemic conditions is counteracted by alpha-lipoic acid. *Archives of biochemistry and biophysics* 324 :85-92.

Hung CC, et al. 2003. Protection of renal epithelial cells against oxidative injury by endoplasmic reticulum stress preconditioning is mediated by ERK1/2 activation. J Biol Chem. 278(31):29317-28. Epub May 8, 2003.

Ivanov, D., G. Dvoriantchikova, A. Pestova, L. Nathanson, and V. I. Shestopalov. 2005. Microarray analysis of fiber cell maturation in the lens. *FEBS letters* 579: 1213-1219.

Janoria, K. G., S. Hariharan, D. Paturi, D. Pal, and A. K. Mitre. 2006. Biotin uptake by rabbit corneal epithelial cells: role of sodium-dependent multivitamin transporter (SMVT). *Current eye research* 31: 797-809.

Jimenez-Orozco, F. A., J. S. Lopez-Gonzalez, A. Nieto-Rodriguez, M. A. Velasco-Velasquez, J. A. Molina-Guameros, N. Mendoza-Patino, M. J. Garcia-Mondragon, P. Elizalde-Galvan, F. Leon-Cedeno, and J. J. Mandoki. 2001, Decrease of cyclin D1 in the human lung adenocarcinoma cell line A-427 by 7-hydroxycoumarin, *Lung cancer* (Amsterdam, Netherlands) 34: 185-194.

Johansson M. and M. Lundberg. 2007. Glutathionylation of beta-actin via a cysteinyl sulfenic acid intermediary. *BMC Biochem* 8: 26.

Jones, D. P., Y. M. Go, C. L. Anderson, T. R. Ziegler, J. M. Kinkade, Jr., and W. G. Kirlin, 2004. Cysteine/cystine couple is a newly recognized node in the circuitry for biologic redox signaling and control. *Faseb J* 18: 1246-1248.

Jung MY, et al. 2001. Chemopreventive allylthiopyridazine derivatives induce apoptosis in SK-Hep-1 hepatocarcinoma cells through a caspase-3-dependent mechanism. Eur J Cancer 37(16):2104-10.

Jürgen, W. 2007. Synthesis and investigations derivatives of (6-hydroxy-3-oxo-3H-xanthen-9-yl)methyl derivatives. A new photoremoveable protecting group. Inaugural Dissertation at Universität Basel.

Kahn, J., P. Preis, F. Waldman, and A. Tseng, Jr. 1994. Coumarin modulates the cell-cycle progression of an MTV-EJras cell line. *Journal of cancer research and clinical oncology* 120 Suppl: S19-22.

Kao, J.P.Y. 2008. Caged Molecules: Principles and Practical Considerations. Current Protocols in Neuroscience. 8.20.1-6.20.21.

Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodation? *Nature* 285: 506-508.

Kim DH, et al. 2005. Aqueous penetration and biological activity of moxifloxacin 0.5% ophthaimic solution and gatifloxacin 0.3% solution in cataract surgery patients. Ophthalmology 112(11):1992-6. Epub Sep. 23, 2005.

Konrad, D., R. Somwar, G. Sweeney, K. Yaworsky, M. Hayashi, T. Ramlal, and A. Klip. 2001. The antihyperglycemic drua alpha-lipoloic acid stimulates glucose uptake via both GLUT4 translocation and GLUT4 activation: potential role of p38 mitogen-activated protein kinase in GLUT4 activation. *Diabetes* 50: 1464-1471.

Krueger, R.R, et al. "Experimental increase in accommodative potential after neodymium: yttrium-aluminum-garnet laser photodisruption of paired cadaver lenses" Ophthalmology (2001) 108(11):2122-29.

Krumdieck, C.L., et al. "Mechanism of Homocysteine Toxicity on Connective Tissues: Implications for the Morbidity of Aging" J. Nutr. (2000) 130:365S-68S.

Kumar RV, et al. 1991: The nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella. 1988. An ultrastructural analysis of plasma membrane in the U18666A cataract. *Investigative ophthalmology & visual science* 29: 261-267.

Lacy, A., and R. O'Kennedy. 2004. Studies on coumarins and coumarin-related compounds to determine their therapeutic role in the treatment of cancer. *Current pharmaceutical design* 10: 3797-3811.

Larsson, H. P., A. V. Tzingounis, H. P. Koch, and M. P. Kavanaugh. 2004. Fluorometric measurements of conformational changes in glutamate transporters. *Proceedings of the National Academy of Sciences of the United States of America* 101: 3951-3956.

Lee V & Bundgaard H. 1992. Improved Ocular Drug Delivery with Prodrugs. In: Sloan K. ed. Prodrugs: Topical and Ocular Delivery, vol. 53, p. 233.

Lesinski L. & Duschmalé J. 2006. Flash Photolysis in Praktikum "Physikalisce Chemie" pp. 1-8.

Li, L., J. Lim, M. D. Jacobs, J. Kistler, and P. J. Donaldson 2007. Regional differences in cystine accumulation point to a sutural delivery pathway to the lens core. *Investigative ophthalmology & visual science* 48: 1253-1260.

Lim, J., Y. C. Lam, J. Kistler, and P. J. Donaldson. 2005. Molecular characterization of the cystine/glutamate exchanger and the excitatory amino acid transporters in the rat lens. *Investigative ophthalmology & visual science* 46: 2869-2877.

Lim, J., L. Li, M. D. Jacobs, J. Kistler, and P. J. Donaldson. 2007. Mapping of glutathione and its precursor amino acids reveals a role

(56) References Cited

OTHER PUBLICATIONS for GLYT2 in glycine uptake in the lens core. *Investigative ophthalmology & visual science* 49: 5142-5151.
Lindsey Rose, K. M., R. G. Gourdie, A. R. Prescott, R. A. Quinian, R. K. Crouch, and K. L. Schey. 2006, The C terminus of lens aquaporin 0 interacts with the cytoskeletal proteins filensin and CP49. *Investigative ophthalmology & visual science* 47: 1562-1570.
Liu H, et al. 1997. Endoplasmic reticulum chaperones GRP78 and calreticulin prevent oxidative stress, Ca2+ disturbances, and cell death in renal epithelial cells. J. Biol Chem. 272(35):21751-9.
Liu, J., E. Head, A. M. Gharib, W. Yuan, R. T. Ingersoll, T. M. Hageb, C. W. Cotman, and B. N. Ames. 2002. Memory loss in old rats is associated with brain mitochondrial decay and RNA/DNA oxidation: partial reversal by feeding acetyl-L-carnitine and/or R-alpha -lipoic acis. *Proceedings of the National Academy of Sciences of the United States of America* 99: 2356-2361.
Lopez-Gonzalez, J. S., H. Prado-Garcia, D. Aguilar-Cazares, J. A. Molina-Guarneros, J. Morales-Fuentes, and J. J. Mandoki. 2004. Apoptosis and cell cycle disturbances induced by coumarin and 7-hydroxycoumarin on human lung carcinoma cell lines. *Lung cancer* (Amsterdam, Netherlands) 43 : 275-283.
Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. *Mol Pharm* 3: 329-339.
Maitra, I., E. Serbinova, H. J. Tritschler, and L. Packer. 1996. Stereospecific effects of R-lipoic acid on buthionine sulfoximine-induced cataract formation in newborn rats. *Biochemical and biophysical research communications* 221: 422-429.
Maitra, I., E. Serbinova, H. Trischler, and L. Packer. 1995. Alpha-lipoic acid prevents buthionine sulfoximine-induced cataract formation in newborn rats. *Free radical biology & medicine* 18: 823-829.
Manns, F., J. M. Parel, D. Denham, C. Billotte, N. Ziebarth D. Borja, V. Fernandez, M. Aly, E. Arrieta, A. Ho, and B. Holden. 2007. Optomechanical response of human and monkey lenses in a lens stretcher. *Investigative ophthalmology & visual science* 48: 3260-3268.
Merdes, A., M. Brunkener, H. Horstmann, and S. D. Georgatos. 1991. Filensin: a new vimentin-binding, polymerization-competent, and membrane-associated protein of the lens fiber cell. *The Journal of cell biology* 115: 397-410.
Merdes, A., F. Gounari, and S. D. Georgatos. 1993. The 47-kD lens-specific protein phakinin is a tailless intermediate filament protein and an assembly partner of filensin. *The Journal of cell biology* 123: 1507-1516.
Moffat, B.A., et al. "Age-related Changes in the Kinetics of Water Transport in Normal Human Lenses" Exp. Eye Res. (1999) 69(6):663-69.
Moini, H., O. Tirosh, Y. C. Park, K. J. Cho, and L. Packer. 2002, R-alpha-lipoic acid action on cell redox status, the insulin receptor, and glucose uptake in 3T3-L1 adipocytes. *Archives of biochemistry and biophysics* 397: 384-391.
Muchowski, P. J., M. M. Valdez, and J. I. Clark. 1999. AlphaB-crystallin selectively targets intermediate filament proteins during thermal stress. *Investigative ophthalmology & visual science* 40: 951-958.
Musk SR, et al. 1997. Cytotoxicity and gehotoxioity of diallyl sulfide and diallyl disulfide towards Chinese hamster ovary cells. Food Chem Toxicot. 35(3-4):379-85.
Newell. 1996. Ophthalmology: Principles and Concepts St. Louis: Mosby-Year Book St. Louis, p. 83.
Obrosova I, et al. 1998. Diabetes-induced changes in lens antioxidant status, glucose utilization and energy metabolism: effect of DL-alpha-lipoic acid. Diabetologia 41(12):1442-50.
Ong, M. D., D. M. Payne, and M. H. Garner, 2003. Differential protein expression in lens epithelial whole-mouths and lens epithelial cell cultures. *Experimental eye research* 77: 35-49.
Pau, H., and J. Kranz 1991. The increasing sclerosis of the human lens with age and its relevance to accommodation and presbyopia.

*Graefe's archive for clinical and experimental ophthalmology = Albrecht von Graefes Archly fur klinische und experimentelle Ophthalmologie* 229: 294-296.
Petit PX, et al. 1995. Alterations in mitochondrial structure and function are early rents of dexamethasone-induced thymocyte apoptosis. J Cell Biol. 130(1):157-67.
Phelps-Brown, N.A., et al. "Nutritional supplements and the eye" Eye (1998) 12:127-33.
Pierscionek, B. K. 1995. Age-related response of human lenses to stretching forces. *Experimental eye research* 60: 325-332.
Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast cancer cell growth by inhibiting ErbB-2 and ERK1. *Bioorganic & medicinal chemistry* 13: 3141-3147.
Salvioli S, et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.
Sandilands, A., A. R. Prescott, A. M. Hutcheson, R. A. Quinlan, J. T. Casselman, and P. G. FitzGeraid, 1995. Filensin is proteolytically processed during lens fiber cell differentiation by multiple independent pathways. *European journal of cell biology* 67: 238-253.
Sarraf D & Lee DA. 1994. The Role of Iontophoresis in Ocular Drug Delivery. J Ocul Pharmacol 10(1):69-81.
Sato, H., M. Tamba, K. Kuriyama-Matsumara, S. Okuno, and S. Bannai. 2000. Molecular cloning and expression of human xCT, the light chain of amino acid transport system xc. *Antioxid Redox Signal* 2: 665-671.
Sato, H., M. Tamba, T. Ishii, and S. Bannai. 1999. Cloning and expression of a plasma membrane cystine/glutamate exchange transporter composed of two distinct proteins. *The Journal of biological chemistry* 274: 11455-11458.
Sato, H., A. Shiiya. M. Kimata, K. Maebara, M. Tamba, Y. Sakakura, N. Makino, F. Sugiyama, K. Yagami, T. Moriguchi, S. Takahashi, and S. Bannai, 2005. Redox imbalance in cystine/glutamate transporter-deficient mice, *The Journal of biological chemistry* 280: 37423-37429.
Schonheit, K., L. Gille, and H. Nohl. 1995. Effect of alpha-lipoic acid and dihydrolipoic acid on ischemia/reperfusion injury of the heart and heart mitochondria. *Biochimica et biophysica acta* 1271: 335-342.
Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.
Shembekar, V. R., Y. Chen, B. K. Carpenter, and G. P. Hess. 2005. A protecting group for carboxylic acids that can be photolyzed by visible light. *Biochemistry* 44: 7107-7114.
Spector, A., et al. "Thioredoxin fragment 31-36 is reduced by dihydrolipoamide and reduces oxidized protein" Biochem Biophys Res Commun (Jan. 1988) 150(1):156-62.
Strenk, S. A., L. M. Strenk, J. L. Semmlow, and J. K. DeMarco. 2004. Magnetic resonance imaging study of the effects of age and accommodation on the human lens cross-sectional area. *Investigative ophthalmology & visual science* 45: 539-545.
Sundaram SG & Milner JA. 1996. Diallyl disulfide suppresses the growth of human colon tumor cell xenografts in athymic nude mice. J Nutr. 126(5):1355-61.
Sweeney, M. H., and R. J. Truscott. 1998. An impediment to glutathione diffusion in older normal human lenses: a possible precondition for nuclear cataract. *Experimental eye research* 87: 587-595.
Tamm, E., E. Lutjen-Drecoll, W. Jungkunz, and J. W. Rohen. 1991. Posterior attachment of ciliary muscle in young, accommodating old, presbyopic monkeys. *Investigative ophthalmology & visual science* 32: 1678-1692.
Tamm, S., E. Tamm, and J. W. Rohen. 1992. Age-related changes of the human ciliary muscle. A quantitative morphometric study. *Mechanisms of ageing and development* 62: 209-221.
Truscott, R. J. 2000. Age-related nuclear cataract: a lens transport problem. *Ophthalmic research* 32: 185-194.

(56) References Cited

OTHER PUBLICATIONS

Wang, C. J., Y. J. Hsieh, C. Y. Chu, Y. L. Lin, and T. H. Tseng. 2002. Inhibition of cell cycle progression in human leukemia HL-60 cells by esculetin. *Cancer letters* 183: 163-168.

Wang, S. J., and H. H. Chen. 2007. Presynaptic mechanisms underlying the alpha-lipoic acid facilitation of glutamite exocytosis in rat cerebral cortex nerve terminals. *Neurochemistry international* 50: 51-60.

Weeber, HA et al. 2007. Stiffness gradient in the crystalline lens. Graefes Arch Clin Exp Ophthalmol 245(9):1357-66.

Widomska, J., M. Raguz, J. Dillon, E. R. Gaillard, and W. K. Subczynski. 2007. Physical properties of the lipid bilayer membrane made of the calf lens lipids: EPR spin labeling studies. *Biochimica et biophysica acta* 1768: 1454-1465.

Wieboldt, R. et al. 1994. Photolabile precursors of glutamate: Synthesis, chemical properties, and activation of glutamate receptors on a microsend time scale. Proc. Natl. Acad. Sci, 91:8752-8756.

Willner I & Zahavy E. 1994. Activation of Glutathione Reductase by Light: A Novel Approach to Design Redox Photo-Enzymes. Angew Chem Int Ed Engl 33(5):581-83.

Yin MC, et al. 2002. Nonenzymatic antioxidant of four organosulfur compounds derived from garlic. J Agric Food Chem. 50(21):6143-7.

Yu, N. T., D. C. DeNagei, P. L. Pruett, and J. F. Kuck, Jr. 1985. Disulfide bond formation in the eye lens. *Proceedings of the National Academy of Sciences of the United States of America* 82: 7965-7968.

Zhao, Y., Q. Zheng, K. Dakin, K. Xu, M. L. Martinez, and W. H. Li. 2004. New caged coumarin fluorophores with extraordinary uncaging cross sections suitable for biological imaging applications. *Journal of the American Chemical Society* 126: 4653-4663.

Zivkovic, D. 2007. Investigations on 2,7-diamino-9-fluorenol photochemistry. Inaugural Dissertation at Universität Basel.

Aloisi et al. 1948. Glycerylphosphorylcholine and Choline Glycerophosphate. Biochemical Journal. vol. 43, pp. 157-161; p. 157, col. 1, para 2-3; col. 2, para 1; p. 158, col. 1, para 4.

Gilbert, Basic Concepts in Biochemistry USA. McGraw Hill 2000 p. 184.

Jablonski et al. Plant Physiology 1978 61:221-225.

Ng et al. Experimental Eye Research 1986 43:477-489.

Morris Jr. Recent advances in arginine metabolism; roles and regulation of the arginases. British Journal of Pharmacology, E-Pub Jun. 5, 2009, 157(6):922-930.

PubChem Compound Summary CID 863 lipoamide (Sep. 16, 2004) (Retrieved from the Internet Nov. 13, 2010; http://pubchem.ncbi.nlm.nih.gov/summary/summary.cgi?cid=863.

Salceda, et al. L-arginine uptake in normal and diabetic rat retina and retinal pigment epithelium. Neurochem Res., 2008, 33(8):1541-1545.

Stuehr et al. Nw-Hydroxy-L-arginine is an intermediate in the Biosynthesis of nitric Oxide from L-Arginine. The Journal of Biological Chemistry 1991, 266(10):6259-6263.

Truscott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.

JP Office Action in JP2007-537922.

Extended European Search Report received in the related European application No. 10790038.3.

Office Communication received in the related Mexican Application No. MX/a/2007/004775.

Extended Search Report corresponding to the European application No. 09825441.0.

Office Action received in U.S. Appl. No. 12/815,586 dated May 9, 2012.

Office Action mailed Mar. 13, 2012, in U.S. Appl. No. 12/815,586, inventors Garner et al., filed Jun. 15, 2010.

Office Action mailed May 9, 2012, in U.S. Appl. No. 12/815,586, inventors Garner et al., filed Jun. 15, 2010.

Office Action mailed Jan. 30, 2013, in U.S. Appl. No. 12/815,586, inventors Garner et al., filed Jun. 15, 2010.

Notice of Allowance mailed Aug. 22, 2012, in U.S. Appl. No. 12/815,586, inventors Garner et al., filed Jun. 15, 2010.

Notice of Allowance mailed Jul. 11, 2013, in U.S. Appl. No. 12/815,586, inventors Garner et al., filed Jun. 15, 2010.

Notice of Allowance mailed Dec. 19, 2013, in U.S. Appl. No. 12/815,586, inventors Garner et al., filed Jun. 15, 2010.

Notice of Allowance mailed Apr. 9, 2014, in U.S. Appl. No. 12/815,586, inventors Garner et al., filed Jun. 15, 2010.

Co-Pending U.S. Appl. No. 14/170,116 inventors Garner et al., filed Jan. 31, 2014.

LOW DOSE LIPOIC AND PHARMACEUTICAL COMPOSITIONS AND METHODS

CROSS-REFERENCE TO RELATED APPLICATIONS

This application claims the benefit of U.S. Provisional Patent Application 61/033,870 filed Mar. 5, 2008, U.S. Provisional Patent Application 61/060,487 filed Jun. 11, 2008, and U.S. Provisional Patent Application 61/077,186 filed Jul. 1, 2008, each of which is incorporated herein by reference in its entirety.

BACKGROUND OF THE INVENTION

As we age, our lenses undergo physiological changes that make it more difficult to focus on near objects. That is why nearly everyone requires reading glasses, even as early as age 35-40. The ability of the eye to change focal power, also known as accommodative amplitude, decreases significantly with age. The accommodative amplitude is 20 diopters in children and young adults, but it decreases to 10 diopters by age 25 and to ≤1 diopter by age 60. The age-related inability to focus on near objects is called presbyopia. All of us will develop presbyopia and will use corrective lenses unless a new treatment is found.

Both presbyopia and cataract are age-related and may share common etiologies such as lens growth, oxidative stress, and/or disulfide bond formation.

There is a need for compositions and methods for combating presbyopia and/or cataract, particularly compositions and methods that minimize toxicity to surrounding healthy tissues.

BRIEF SUMMARY OF THE INVENTION

In one embodiment, a pharmaceutical composition for ocular use comprises a lipoic acid-based active agent and a pharmaceutically acceptable carrier. The amount of the active agent can be, e.g., less than about 250 µM, about 5 µM to about 250 µM, or about 10 µM to about 100 µM. The pharmaceutical composition can include, e.g., an emulsifier and a buffered carrier.

The active agent can be, e.g., any one of 5-(1,2-dithiolan-3-yl)pentanoic acid; 5-(1,2-thiaselenolan-5-yl)pentanoic acid; dihydrolipoate; 5-(1,2-thiaselenolan-3-yl)pentanoic acid; 6,8-dimercaptooctanoic acid; or a salt or ester thereof. The active agent can be the R enantiomer.

In another embodiment, a method of preventing or treating oxidation damage to cells comprises administering the pharmaceutical composition either in vivo or in vitro. The cells can be ocular cells, e.g., lens cells. The compound can be administered via a topical ocular, subtenons, subconjunctival, intracameral, intravitreal, or iontophoresis route.

The method can include a step of administering a chemical energy source, e.g., glucose or NADPH, simultaneously or consecutively with the active agent. The method can include a step of applying energy, e.g., to a localized region, to facilitate breaking disulfide bonds.

The method can be used to increase or maintain accommodative amplitude, as measured in diopters, to at least 2% greater than the accommodative amplitude expected in an untreated lens of about the same age. The method can increases accommodative amplitude by at least 0.25 diopters. The method can be used to increase or maintain lens elasticity, as measured in diopters or by elasticity E, to at least 2% greater than the elasticity expected in an untreated lens of about the same age. The method can be used to decrease or maintain lens opacity to at least 2% less than the opacity expected in an untreated lens of about the same age.

DETAILED DESCRIPTION OF THE INVENTION

Figure 1:
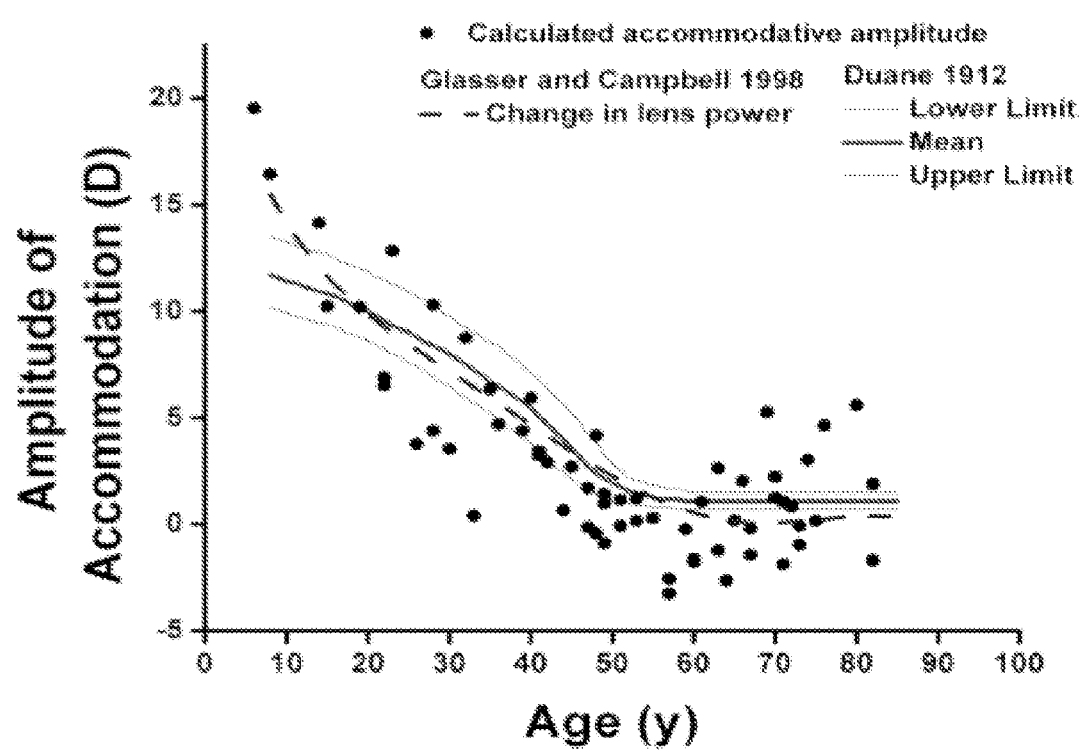
FIG. 1 depicts the accommodative amplitude in diopters (D) of an untreated human lens as a function of age in years. Borja, D et al. 2008. Optical Power of the Isolated Human Crystalline Lens. Invest Ophthalmol Vis Sci 49(6):2541-8. Borja et al. calculated the maximum possible accommodative amplitude of each measured lens power data point (n=65). As shown, there is good agreement between the age-dependent loss of accommodation and the maximum amplitude of accommodation calculated from the isolated lens power.

Compositions and methods are provided that can prevent, reduce, reverse, and/or slow the rate of lens growth, oxidative damage, and/or disulfide bond formation. These compositions and methods may thus effectively prevent or treat presbyopia and/or cataract.

In one embodiment, we provide a pharmaceutical composition comprising an active agent that is lipoic acid, especially alpha lipoic acid, or a derivative thereof. Preferably, the active agent is a reducing agent that is capable of reducing disulfide bonds, particularly disulfide bond formation in lens membranes and membrane associated proteins. Accordingly, particularly preferred active agents are capable of entering into the lens epithelial cells.

In one embodiment, the active agent enters the lens epithelial cells using a naturally occurring transport mechanism. For example, lipoic acid enters lens cells via specific plasma membrane symporters and antiporters. In one embodiment, the active agent is a derivative of lipoic acid that maintains the capability of utilizing the naturally occurring transport mechanism for lipoic acid.

In one embodiment, the active agent is lipoic acid, especially alpha-lipoic acid, or a derivative thereof. Lipoic acid-based active agents include, but are not limited to, 5-(1,2-dithiolan-3-yl)pentanoic acid (lipoic acid); 6,8-dimercaptooctanoic acid (dihydrolipoic acid); and dihydrolipoate.

In another embodiment, the active agent can be a seleno-substituted agent. Without being bound by theory, it is believed that including selenium in the active agent can improve redox potential compared to the same agent without selenium. The selenium derivative can thus take advantage of the intracellular redox potential of the lens. Accordingly, the active agent can be a lipoic acid derivative including selenium. In one embodiment, the active agent is a seleno-lipoic acid-based agent such as 5-(1,2-thiaselenolan-5-yl)pentanoic acid or 5-(1,2-thiaselenolan-3-yl)pentanoic acid.

In one embodiment, the active agent is 5-(1,2-dithiolan-3-yl)pentanoic acid; 6,8-dimercaptooctanoic acid; dihydrolipoate; 5-(1,2-thiaselenolan-5-yl)pentanoic acid; or 5-(1,2-thiaselenolan-3-yl)pentanoic acid. In another embodiment, the active agent is 6,8-dimercaptooctanoic acid; dihydrolipoate; 5-(1,2-thiaselenolan-5-yl)pentanoic acid; or 5-(1,2-thiaselenolan-3-yl)pentanoic acid. In another embodiment, the active agent is 6,8-dimercaptooctanoic acid or dihydrolipoate. In yet another embodiment, the active agent is 5-(1,2-dithiolan-3-yl)pentanoic acid.

The active agent can also be in a salt or ester form.

The active agent can be administered as a racemate or as an enantiomer. Lipoic acid and its derivatives are preferably administered to include the R form. Synthetic methods to yield a racemate may be less expensive than stereo-specific processes including isolation/purification steps. On the other hand, administering a single enantiomer can lower the therapeutically effective amount, thus decreasing any toxicity effects of the active agent.

As the agents described herein may have therapeutic uses as described in further detail below, it is preferable to select an active agent with low toxicity. Additional acceptable lipoic acid derivatives can be selected by in vitro toxicology testing. See Example 1.

The agents described herein can be formulated with a pharmaceutically acceptable carrier to provide pharmaceutical compositions. The pharmaceutical composition may also contain one or more excipients as is well known in the art of pharmaceutical formulary. In one embodiment, the pharmaceutical composition is formulated for ocular use. That is, the pharmaceutically acceptable carrier and/or other excipients are selected to be compatible with, and suitable for, ocular use. Such carriers and excipients are well known in the art.

The excipients may also be selected and/or formulated to improve the solubility of the agent. For example, the pharmaceutical composition can include one or more of emulsifiers, buffers, salts, preservatives, lubricants, polymers, solvents, and other known excipients for ocular pharmaceutical formulations. In one embodiment, the pharmaceutical composition includes an emulsifier and a buffered carrier such as Polysorbate 80 in HBSS (Hank's Balanced Salt Solution).

The agents can also be administered with a chemical energy source, such as portion of glucose or NADPH, to facilitate reduction. The agent and chemical energy source can be co-formulated (e.g., prepared together in a single pharmaceutical formulation) or co-administered (administered simultaneously or consecutively in any order in individual formulations).

In one embodiment, the pharmaceutical composition contains a low dose of the active agent. In one embodiment, the concentration of a lipoic acid-based active agent in the pharmaceutical composition is about 0.0002 to 0.05 weight percent, more preferably about 0.0002 to 0.02, 0.001 to 0.02, or 0.002 to 0.02 weight percent. In another embodiment, the concentration of a lipoic acid-based active agent in the pharmaceutical composition is less than 0.05, 0.02, 0.01, 0.002, 0.001, or 0.0002 weight percent.

Although lipoic acid is a naturally occurring substance in the eye, and exogenous lipoic acid has been used before in various contexts, the present inventors have surprisingly found that a dramatic reduction in formulation and dosing amounts is possible with little if any effect on efficacy. For example, previous attempts to use lipoic acid to improve accommodation required concentrations of 0.05-0.2 weight percent (see U.S. Pat. No. 5,817,630). However, the present inventors have discovered that the concentration may be lowered, in some cases lowered by orders of magnitude, with little if any decrease in efficacy. This discovery has important synthesis, formulation, and toxicity implications. Regarding the synthesis, the formulation and dosing amounts may be further reduced by isolating the R enantiomer as described above. Regarding the formulation, the dosage of the lipoic acid-based active agent can be, e.g., 0.001 to 0.02 weight percent while still maintaining equal efficacy to doses of 1 mM or greater. This demonstrated efficacy in turn reduces any concomitant toxicity, thereby achieving a more desirable safety and efficacy profile. Moreover, when the active agent is used in combination with other active components, such as, e.g., a photolabile protecting group as described in the co-pending U.S. Patent Application describing caged compounds, the ability to reduce the dose of lipoic acid also reduces the dose of the accompanying protecting group. Thus, lowering the dose of the lipoic acid-based active agent achieves a reduction in toxicity for all accompanying components.

The agents described herein can be employed in a method including the step of providing a lipoic acid-based active agent to a cell, either in vitro or in vivo.

The agents described herein can be employed in a method for treating or preventing oxidation damage to cells. Such a method includes the step of administering a pharmaceutical composition comprising a lipoic acid-based active agent to a cell, either in vitro or in vivo.

As stated above, the agents can be delivered to cells in vitro or in vivo. In one embodiment, the cells are in vivo. In either case, the cells can be ocular cells, e.g., lens cells. In one embodiment, the agent is delivered to a lens, either in vitro or in vivo. Because oxidative damage has been implicated in other disorders including cancer, the agents may prove useful for administration to any type of cell exhibiting or prone to oxidative damage.

The agents can be administered to a lens by any route of administration including, but not limited to, topical ocular, subtenons, subconjunctival, intracameral, intravitreal, or iontophoresis routes. In one embodiment, the agent can be delivered topically, e.g., via an eye drop, gel, ointment, or salve. In other embodiment, the agent can be delivered via an acute delivery system, e.g., using nanotubes, local injection, microinjection, syringe or scleral deposition, or ultrasound. The delivery systems can be adapted to delivery the agent to a target region, e.g., an area exhibiting inelasticity, opacity, and/or proliferation. In one embodiment, the agent can be localized to the anterior central portion of the lens.

The method can further include applying energy. Exemplary forms of applied energy include, but are not limited to, laser, ultrasound, tuned and focused ultrasound, particle beam, plasma beam, X-ray, ultraviolet, visible light, infrared, heat, ionizing, light, magnetic, microwave, sound, electrical, femtosecond laser, and tuned femtosecond laser. Additionally or alternatively, the energy can be applied to only a localized area of the target. In some embodiment, energy is applied using an LED or laser source, which advantageously enables spatial specificity to deliver light to a localized region. Additionally or alternatively, other optical tools for creating and/or improving spatial specificity can be used with the methods described herein. The energy can be targeted to particular areas, e.g., areas exhibiting inelasticity, opacity, and/or proliferation, while leaving other areas unaffected. In one embodiment, the energy can be localized to the anterior central portion of the lens. This step can be performed as previously disclosed in co-pending U.S. Publication 2008/0139990 or co-pending U.S. Patent Application describing caged compounds.

The energy can be applied within the "activation volume" to change the flexibility of the lens so that the restoring force of the lens capsule is able to form the lens to a maximal spherical shape with increased curvature. The "activation volume" would be limited only by the available dilation of the patient papillary area although a smaller area may suffice to restore accommodative amplitude.

The methods preferably utilize a therapeutically effective amount of the active agent. The term "therapeutically effective amount" means an amount that is capable of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

Lens elasticity decreases with age, and is a primary diagnostic and causative factor for presbyopia. Lens elasticity can be measured as accommodative amplitude in diopters (D). FIG. 1 depicts the average elasticity in diopters of an untreated human lens as a function of age in years. The lower the value of D, the less elastic the lens. In one embodiment, the agents described herein (in the active form) can decrease and/or maintain D at a value that is greater than the D value exhibited by an untreated lens of about the same age. In other words, the agents can keep accommodative amplitude "above the line" (the solid line mean accommodative amplitude) depicted in FIG. 1. In one embodiment, D is increased and/or maintained at a value about 2, 5, 7, 10, 15, 25, 50, 100, 150, or 200 percent above the line. However, as individual lenses may differ with respect to average values, another embodiment provides any increase in accommodative amplitude, maintenance of accommodative amplitude, or reduction in the rate of decline of accommodative amplitude (i.e., reduction in the rate of decrease in diopters) for an individual lens compared to the accommodative amplitude of the same lens before treatment. Accordingly, in another embodiment, the methods provide an increase in accommodative amplitude of about 0.25 to about 8 diopters, or at least about 0.1, 0.2, 0.25, 0.5, 1, 1.2, 1.5, 1.8, 2, 2.5, 3, 5, or 8 diopters compared to the same lens before treatment.

Figure 2:
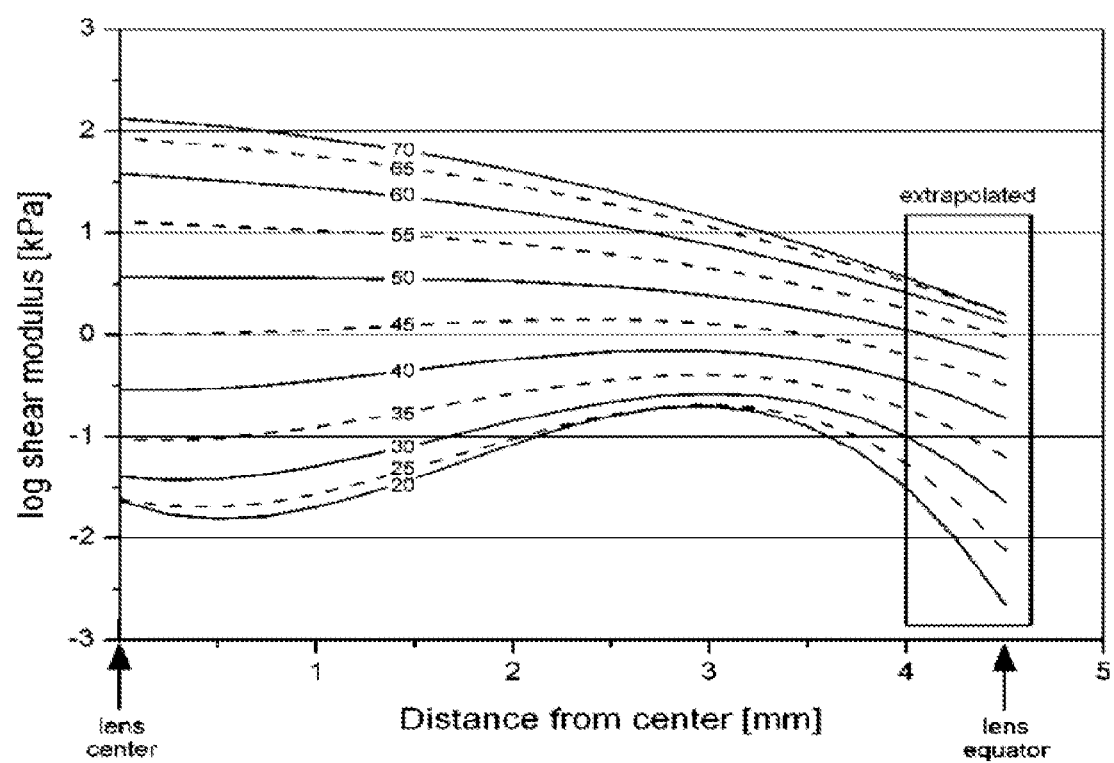
FIG. 2 shows a trend graph of the shear modulus versus position in the lens and age. Weeber, H A et al. 2007. Stiffness gradient in the crystalline lens. Graefes Arch Clin Exp Ophthalmol 245(9): 1357-66. The line at the bottom is the 20-year-old lens; the line at the top is the 70-year-old lens. The modulus increases with age for all positions in the lens. Measurements were taken up to 4.0 mm from the lens centre. The lines are extrapolated to a radius of 4.5 mm (lens diameter 9.0 mm).

Lens elasticity can also be measured by the unit of elasticity E. The higher the value of E, the less elastic the lens. FIG. 2 depicts the average elasticity (E) of an untreated human lens as a function of age in years. In one embodiment, the agents described herein (in the active form) can decrease and/or maintain E at a value that is less than the E value exhibited by an untreated lens of about the same age. In other words, the agents can keep lens elasticity "below the line" depicted in FIG. 2. In one embodiment, E is decreased and/or maintained at a value about 2, 5, 7, 10, 15, 25, 50, 100, 150, or 200 percent below the line. However, as individual lenses may differ with respect to average values, another embodiment provides any increase inelasticity, maintenance of elasticity, or reduction in the rate of decline of elasticity (i.e., reduction in the rate of increase in E value) for an individual lens compared to the elasticity of the same lens before treatment.

Figure 3:
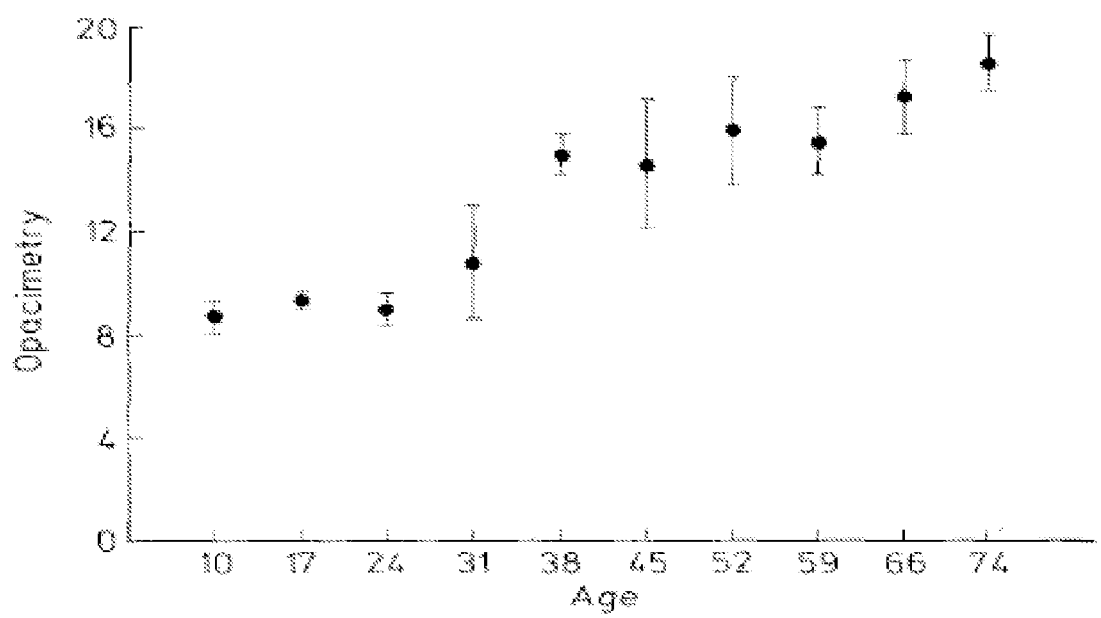
FIG. 3 depicts the average opacity (opacimetry) of an untreated human lens as a function of age in years. Bonomi, L et al. 1990. Evaluation of the 701 interzeag lens opacity meter. Graefe's Arch Clin Exp Ophthalmol 228(5):447-9. Lens opacity was measured in 73 healthy subjects between 10 and 76 years of age without slit-lamp evidence of cataract and with a visual acuity of 20/20. These subjects were classified into ten age groups. This study was carried out using the Interzeag Opacity Meter according to the procedure described by Flammer and Bebies (Flammer J, Bebie H. 1987. Lens Opacity Meter: a new instrument to quantify lens opacity. Ophthalmologica 195(2):69-72) and following the suggestions of the operating manual for the instrument.

Therapeutic efficacy can also be measured in terms of lens opacity. Lens opacity increases with age and is a primary diagnostic and causative factor for cataract. FIG. 3 depicts the average opacity of an untreated human lens as a function of age in years. In one embodiment, the agents described herein (in the active form) can decrease and/or maintain opacity at a value that is less than the opacity value exhibited by an untreated lens of about the same age. In other words, the agents can keep lens opacity "below the line" depicted in FIG. 3. In one embodiment, lens elasticity is decreased and/or maintained at a value about 2, 5, 7, 10, 15, 25, 50, 100, 150, or 200 percent below the line. However, as individual lenses may differ with respect to average values, another embodiment provides any decrease, maintenance, or reduction in the rate of increase of opacity for an individual lens compared to the opacity of the same lens before treatment.

Therapeutic efficacy can also be measured as a reduction in the rate of cell proliferation, particularly lens epithelial cell proliferation. Thus, in some embodiments, therapeutic efficacy can be measured by cytostatic effect.

Some agents described herein exist naturally in the untreated eye. Lipoic acid, for example, occurs naturally in eye tissue. In general, a therapeutically effective amount of the exogenously administered agent is often at least about 1 or 2 orders of magnitude larger than the natural level of the compound. In one embodiment, the dose amount of lipoic acid or a derivative thereof is about 5 µM to about 250 µM or about 10 µM to about 100 µM. In another embodiment, the dose amount of lipoic acid or derivative thereof is no more than about 250 µM, 100 µM, 50 µM, 20 µM, 10 µM. The dose amount will depend on the route of administration as well as the age and condition of the patient. Similarly, the frequency of dosing will depend on similar factors as can be determined by one of ordinary skill in the art.

Efficacy has been demonstrated in vitro for specific exemplary dosing. (See Example 2) FIG. 2 shows that the inelasticity increases by a factor of nearly 20 during the critical period from age 40 to 55 years. From current data, a 10 µM dose can decrease the inelasticity over 95% within a millimeter volume element (voxel). Extrapolation of these results to a volume element in the human lens suggests that using this treatment dose on a 55 year old person with a 10 kPA lens starting modulus value (see FIG. 2) could be reduced after treatment to a value of about 0.5 kPA (which then corresponds to a value typically seen with a 40 yr old person). FIG. 1 permits a conversion of these modulus values to optical amplitude: accommodative amplitude is normally reduced to almost 0 above 55 years, while a person at 40-45 years still exhibits around 4-5 diopters of accommodation.

The methods include preventative methods that can be performed on patients of any age. The methods also include therapeutic methods that can be performed on patients of any age, particularly patients that are 20, 25, 30, 35, 40, 45, 50, 52, 55, 57, 60, 70, 75, or 80 years of age or older.

Any numerical values recited herein include all values from the lower value to the upper value in increments of any measurable degree of precision. For example, if the value of a variable such as age, amount, time, percent increase/decrease and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

EXAMPLES

Example 1

In Vitro Toxicology Studies

Cell viability was determined using human umbilical vein endothelial cells (HUVEC, first passage). Cells were treated with the active agent in doses ranging from 0.1 µM to 100 µM. The number of live and dead cells was determined using the MultiTox-Fluor assay (Promega) or Live/Dead® assay (Invitrogen). Logistic plots were used to determine the compound's $LD_{50}$ value. Lipoic acid was not cytotoxic in the concentration range.

Example 2

In Vitro Efficacy Studies

Increase in Elasticity:

Pairs of mouse lenses were incubated in medium 200 supplemented with an antibiotic, an antimycotic, in the presence or absence of lipoic acid (concentrations ranging from 0.5 µM to 500 µM) for 8-15 hours. Each lens was removed from medium, weighed, and photographed on a micrometer scale. A coverslip of known weight (0.17899±0.00200 g) was placed on the lens, and the lens was photographed again on the micrometer scale. The diameter of each lens with and without the coverslip was determined from the photographs. The change in lens diameter produced by the force (coverslip) was computed $\Delta D=(D_{withcoverslip}-D_{withoutcoverslip})$. The results (FIG. 4, ‡) indicate that lipoic acid at concentrations≥9.6 µM caused a statistically significant increase in ΔD, p<0.0001.

Figure 4:
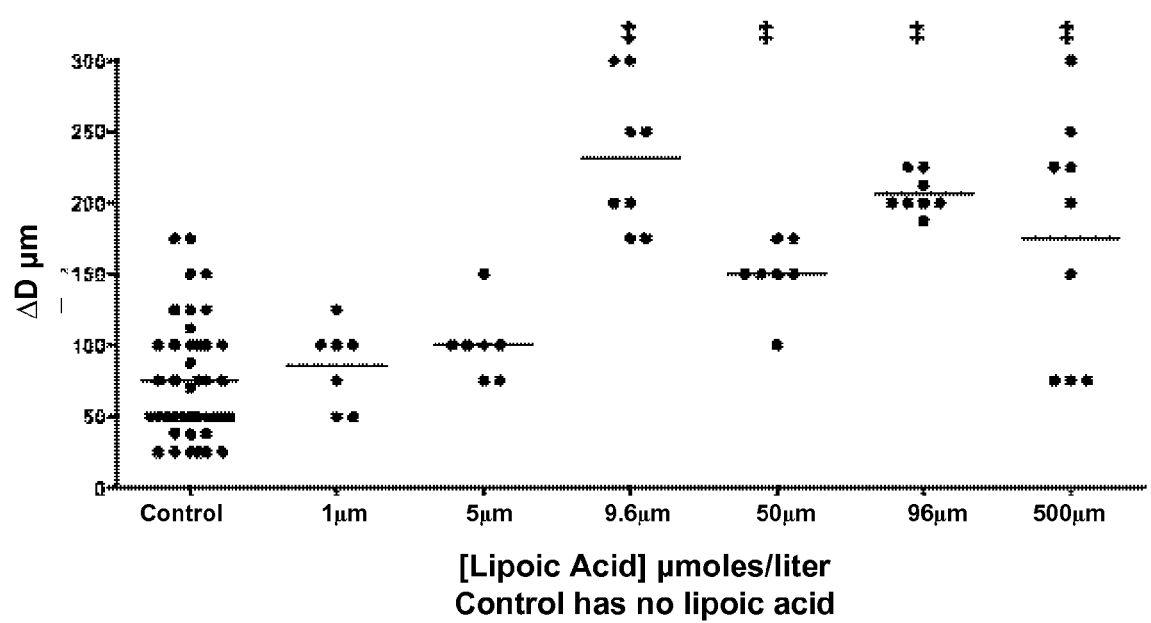
FIG. 4 depicts a scatter plot of the change in ΔD (micrometers) in the absence (control) and presence of lipoic acid in lens organ culture experiments. The symbol ‡ designates significantly larger changes in ΔD when compared to controls. Statistical values are highly significant at p<0.0001 by unpaired t-test and by Kiruskal Wallis test, which compared medians of each data set. The relative change in Young's modulus (E) can be calculated as the cubic value derived from the ΔD of the control divided by the ΔD of the experimental or E fractional change=(ΔD con/ΔDexp)^3.
Figure 5:
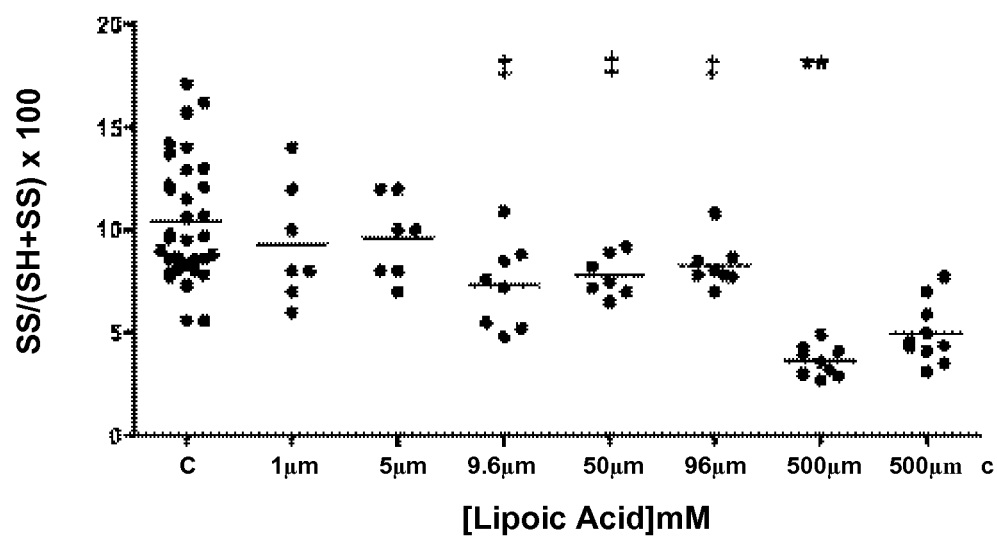
FIG. 5 depicts a scattergram of the percent of the total protein SH groups in disulfide bonds. Free SH groups were alkylated with 4-acetamido-4'-maleimidylstilbene-2,2'-sulfonic acid (c, 1 µM, 5 µM, 9.6 µM, 50 µM, 96 µM) or 7-diethylamino-3-(4'maleimidylphenyl)-4-methyl coumarin (500 µM, and 500 µM c). Following removal of the first alkylating agent, the S—S bonds were reduced and alkylated with fluorescein-5-maleimide. Absorption spectra were used to calculated total protein (A280 nm), free protein SH (A322 or A384), and protein SS (A490) using the appropriate extinction coefficients. The symbol ‡ indicates statistically significant difference of mean with mean of control (c, p≤0.05). The symbol ** indicates means of 500 µM lipoic acid and the 500 µM control were significantly different from each other (p=0.027).

Decrease in Disulfide Bonds:

Lipoic acid at concentrations≥9.6 µM caused a statistically significant decrease in protein disulfides in the mouse lenses where there was a significant increase in ΔD (FIG. 4). Mouse lenses were homogenized in a denaturing buffer containing a fluorescent alkylating agent to modify the free SH groups. After removing the alkylating agent homogenates were reduced and alkylated with a different fluorescent alkylating agent. Absorption spectra of the modified proteins were used to calculate free protein SH and protein SS groups. The results are shown in FIG. 5.

Example 3

Preclinical and Clinical Studies

An exemplary clinical protocol may include patient selection criteria of age 45-55 years with some loss of clinical accommodative amplitude.

A test compound and/or placebo control may be administered in a controlled dark sterile environment with 1-photon visible light LED (computer controlled tilt mirror) system.

For acute treatment, the clinician could 1) apply a topical mydriatic agent, 2) wait for pupillary dilation (about 5 minutes), 3) introduce a test compound and/or placebo control with an appropriate delivery device, 4) wait 30 minutes, and 5) apply topical agent (e.g., cholecystokinin and vasopressin) to retract iris sphincter muscle to aid release of zonular tension during lens cytosol protein remolding.

Immediately following the procedure, the clinician may allow a time period for ocular drug clearance (e.g., about 30-60 minutes) and then allow patient to go home with laser glasses having a cutoff filter of about >550 nm.

For post-operative follow-up in about 1 day to 1 week, the clinician may evaluate the treatment modality for a desired visual endpoint, e.g., accommodative amplitude or elasticity.

The procedure can be repeated to gain further efficacy (e.g., to obtain 2 D in patients older than 55 years) and/or to restore near vision (depending on the duration of action).

A similar protocol could be adapted for preclinical testing animal in vivo lens models.

The examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:

1. A pharmaceutical composition for ocular use comprising an active agent selected from the group consisting of:
   5(1,2-dithiolan-3-yl)pentanoic acid;
   6,8-dimercaptooctanoic acid;
   dihydrolipoate;
   a salt thereof, and an ester thereof, in an amount from about 5 µM to about 250 µM and at least one pharmaceutically acceptable carrier.

2. The pharmaceutical composition of claim 1, wherein the active agent is present in an amount of about 10 µM to about 100 µM.

3. The pharmaceutical composition of claim 1, wherein the active agent is 5-(1,2-dithiolan-3-yl)pentanoic acid or a salt or ester thereof.

4. The pharmaceutical composition of claim 1, wherein the active agent is the R enantiomer.

5. The pharmaceutical composition of claim 1, comprising an emulsifier and a buffered carrier.

6. The pharmaceutical composition of claim 1, wherein the active agent is present in an amount of about 10 μM to about 50 μM.

* * * * *